(12) United States Patent
Ashton

(10) Patent No.: US 8,252,307 B2
(45) Date of Patent: Aug. 28, 2012

(54) METHOD FOR TREATING AND/OR PREVENTING RETINAL DISEASES WITH SUSTAINED RELEASE CORTICOSTEROIDS

(75) Inventor: Paul Ashton, Newton, MA (US)

(73) Assignee: pSivida US, Inc., Watertown, MA (US)

( * ) Notice: Subject to any disclaimer, the term of this patent is extended or adjusted under 35 U.S.C. 154(b) by 97 days.

(21) Appl. No.: 12/684,341

(22) Filed: Jan. 8, 2010

(65) Prior Publication Data

US 2010/0168073 A1 Jul. 1, 2010

Related U.S. Application Data

(63) Continuation of application No. 11/635,161, filed on Dec. 7, 2006, now abandoned, which is a continuation of application No. 10/253,825, filed on Sep. 25, 2002, now abandoned, which is a continuation of application No. 09/735,636, filed on Dec. 14, 2000, now Pat. No. 6,548,078, which is a continuation of application No. 09/273,548, filed on Mar. 22, 1999, now Pat. No. 6,217,895.

(51) Int. Cl.
*A61F 2/00* (2006.01)

(52) U.S. Cl. ...................................... 424/427

(58) Field of Classification Search .................. None
See application file for complete search history.

(56) References Cited

U.S. PATENT DOCUMENTS

| | | | |
|---|---|---|---|
| 3,416,350 A | 12/1968 | Ness | |
| 3,618,604 A | 11/1971 | Ness | |
| 3,630,200 A | 12/1971 | Higuchi | |
| 3,632,739 A | 1/1972 | Kornblum | |
| 3,829,570 A | 8/1974 | Heider et al. | |
| 3,854,480 A | 12/1974 | Zaffaroni | |
| 3,896,819 A | 7/1975 | Zaffaroni et al. | |
| 3,916,899 A | 11/1975 | Theeuwes et al. | |
| 3,948,254 A | 4/1976 | Zaffaroni | |
| 3,961,628 A | 6/1976 | Arnold | |
| 3,977,404 A | 8/1976 | Theeuwes | |
| 3,980,463 A | 9/1976 | Muramoto et al. | |
| 3,993,071 A | 11/1976 | Higuchi et al. | |
| 4,008,719 A | 2/1977 | Theeuwes et al. | |
| 4,014,334 A | 3/1977 | Theeuwes et al. | |
| 4,014,335 A | 3/1977 | Arnold | |
| 4,034,758 A | 7/1977 | Theeuwes | |
| 4,036,227 A | 7/1977 | Zaffaroni et al. | |
| 4,077,407 A | 3/1978 | Theeuwes et al. | |

(Continued)

FOREIGN PATENT DOCUMENTS

CA  2544460 A1  5/2001

(Continued)

OTHER PUBLICATIONS

International Search Report for PCT/US2004/035430 dated Aug. 12, 2005.

(Continued)

*Primary Examiner* — Bethany Barham

(74) *Attorney, Agent, or Firm* — Ropes & Gray LLP; David P. Halstead; David P. Pleynet

(57) ABSTRACT

The present invention relates to a method for administering a corticosteroid to a posterior segment of an eye. In the method, a sustained release device is implanted to deliver the corticosteroid to the eye. The aqueous corticosteroid concentration remains less than vitreous corticosteroid concentration during release of the corticosteroid from the device.

25 Claims, 2 Drawing Sheets

U.S. PATENT DOCUMENTS

| | | |
|---|---|---|
| 4,111,201 A | 9/1978 | Theeuwes |
| 4,111,203 A | 9/1978 | Theeuwes |
| 4,135,514 A | 1/1979 | Zaffaroni et al. |
| 4,142,526 A | 3/1979 | Zaffaroni et al. |
| 4,177,256 A | 12/1979 | Michaels et al. |
| 4,186,184 A | 1/1980 | Zaffaroni |
| 4,200,098 A | 4/1980 | Ayer et al. |
| 4,247,498 A | 1/1981 | Castro |
| 4,256,108 A | 3/1981 | Theeuwes |
| 4,260,736 A | 4/1981 | Asano et al. |
| 4,283,394 A | 8/1981 | West et al. |
| 4,290,426 A | 9/1981 | Luschen et al. |
| 4,304,232 A | 12/1981 | Michaels |
| 4,304,765 A | 12/1981 | Shell et al. |
| 4,322,323 A | 3/1982 | Capozza |
| 4,326,525 A | 4/1982 | Swanson et al. |
| 4,327,725 A | 5/1982 | Cortese et al. |
| 4,351,337 A | 9/1982 | Sidman |
| 4,439,196 A | 3/1984 | Higuchi |
| 4,475,916 A | 10/1984 | Himmelstein |
| 4,478,818 A | 10/1984 | Shell et al. |
| 4,484,922 A | 11/1984 | Rosenwald |
| 4,519,801 A | 5/1985 | Edgren |
| 4,519,909 A | 5/1985 | Castro |
| 4,522,625 A | 6/1985 | Edgren |
| 4,609,374 A | 9/1986 | Ayer |
| 4,615,698 A | 10/1986 | Guittard et al. |
| 4,624,847 A | 11/1986 | Ayer et al. |
| 4,627,850 A | 12/1986 | Deters et al. |
| 4,652,441 A | 3/1987 | Okada et al. |
| 4,657,543 A | 4/1987 | Langer et al. |
| 4,673,405 A | 6/1987 | Guittard et al. |
| 4,681,755 A | 7/1987 | Columbo et al. |
| 4,692,336 A | 9/1987 | Eckenhoff et al. |
| 4,693,886 A | 9/1987 | Ayer |
| 4,711,782 A | 12/1987 | Okada et al. |
| 4,716,031 A | 12/1987 | Eckenhoff et al. |
| 4,717,567 A | 1/1988 | Wu et al. |
| 4,720,384 A | 1/1988 | DiLuccio et al. |
| 4,730,013 A | 3/1988 | Bondi et al. |
| 4,740,365 A | 4/1988 | Yukimatsu et al. |
| 4,743,247 A | 5/1988 | Wong |
| 4,764,364 A | 8/1988 | Heller et al. |
| 4,777,049 A | 10/1988 | Magruder et al. |
| 4,786,500 A | 11/1988 | Wong |
| 4,789,513 A | 12/1988 | Cloeren |
| 4,806,382 A | 2/1989 | Goldberg et al. |
| 4,814,323 A | 3/1989 | Andrieu et al. |
| 4,830,860 A | 5/1989 | Ranade |
| 4,832,957 A | 5/1989 | Dempski et al. |
| 4,839,177 A | 6/1989 | Columbo et al. |
| 4,839,342 A | 6/1989 | Kaswan |
| 4,861,627 A | 8/1989 | Mathiowitz et al. |
| 4,863,455 A | 9/1989 | Whitehead |
| 4,863,735 A | 9/1989 | Kohn et al. |
| 4,865,846 A | 9/1989 | Kaufman |
| 4,877,618 A | 10/1989 | Reed, Jr. |
| 4,882,150 A | 11/1989 | Kaufman |
| 4,889,720 A | 12/1989 | Konishi |
| 4,891,223 A | 1/1990 | Ambegaonkar et al. |
| 4,898,733 A | 2/1990 | DePrince et al. |
| 4,913,906 A | 4/1990 | Friedman et al. |
| 4,927,632 A | 5/1990 | Wong |
| 4,927,687 A | 5/1990 | Nuwayser |
| 4,945,089 A | 7/1990 | Clark |
| 4,946,456 A | 8/1990 | Roth et al. |
| 4,952,402 A | 8/1990 | Sparks et al. |
| 4,959,217 A | 9/1990 | Sanders et al. |
| 4,994,273 A | 2/1991 | Zentner et al. |
| 5,028,435 A | 7/1991 | Katz et al. |
| 5,035,891 A | 7/1991 | Runkel et al. |
| 5,088,505 A | 2/1992 | De Nijs et al. |
| 5,091,185 A | 2/1992 | Castillo et al. |
| 5,098,443 A | 3/1992 | Parel et al. |
| 5,102,389 A | 4/1992 | Hauser |
| 5,120,548 A | 6/1992 | McClelland et al. |
| 5,124,392 A | 6/1992 | Robertson et al. |
| 5,141,752 A | 8/1992 | Ayer et al. |
| 5,147,647 A | 9/1992 | Darougar |
| 5,156,623 A | 10/1992 | Hakamatsuka et al. |
| 5,174,999 A | 12/1992 | Magruder et al. |
| 5,201,764 A | 4/1993 | Kelman et al. |
| 5,213,808 A | 5/1993 | Bar-Shalom et al. |
| 5,226,902 A | 7/1993 | Bae et al. |
| 5,294,604 A | 3/1994 | Nussenblatt et al. |
| 5,314,419 A | 5/1994 | Pelling |
| 5,342,622 A | 8/1994 | Williams et al. |
| 5,378,475 A | 1/1995 | Smith et al. |
| 5,389,382 A | 2/1995 | List et al. |
| 5,393,536 A | 2/1995 | Brandt et al. |
| 5,411,952 A | 5/1995 | Kaswan |
| 5,413,572 A | 5/1995 | Wong et al. |
| 5,431,921 A | 7/1995 | Thombre |
| 5,435,998 A | 7/1995 | Abelson |
| 5,443,505 A | 8/1995 | Wong et al. |
| 5,474,979 A | 12/1995 | Ding et al. |
| 5,476,511 A | 12/1995 | Gwon et al. |
| 5,482,934 A | 1/1996 | Calatayud et al. |
| 5,512,293 A | 4/1996 | Landrau et al. |
| 5,543,441 A | 8/1996 | Rhee et al. |
| 5,554,187 A | 9/1996 | Rizzo, III |
| 5,569,429 A | 10/1996 | Luker |
| 5,573,775 A | 11/1996 | Robertson et al. |
| 5,593,697 A | 1/1997 | Barr et al. |
| 5,618,560 A | 4/1997 | Bar-Shalom et al. |
| 5,639,275 A | 6/1997 | Baetge et al. |
| 5,650,170 A | 7/1997 | Wright et al. |
| 5,665,373 A | 9/1997 | Robertson et al. |
| 5,753,234 A | 5/1998 | Lee et al. |
| 5,766,242 A | 6/1998 | Wong et al. |
| 5,770,589 A | 6/1998 | Billson et al. |
| 5,773,019 A | 6/1998 | Ashton et al. |
| 5,830,546 A | 11/1998 | Ehret et al. |
| 5,840,335 A | 11/1998 | Wenzel et al. |
| 5,851,547 A | 12/1998 | Fujioka et al. |
| 5,902,598 A | 5/1999 | Chen et al. |
| 5,989,581 A | 11/1999 | Groenewegen |
| 5,998,431 A | 12/1999 | Tseng et al. |
| 6,039,975 A | 3/2000 | Shah et al. |
| 6,051,576 A | 4/2000 | Ashton et al. |
| 6,120,791 A | 9/2000 | Aguadisch et al. |
| 6,120,802 A | 9/2000 | Breitenbach et al. |
| 6,123,861 A | 9/2000 | Santini, Jr. et al. |
| 6,217,895 B1 | 4/2001 | Guo et al. |
| 6,242,058 B1 | 6/2001 | Bahadur et al. |
| 6,267,154 B1 | 7/2001 | Felicelli et al. |
| 6,283,951 B1 | 9/2001 | Flaherty et al. |
| 6,331,313 B1 | 12/2001 | Wong et al. |
| 6,368,658 B1 | 4/2002 | Schwarz et al. |
| 6,375,972 B1 | 4/2002 | Guo et al. |
| 6,441,047 B2 | 8/2002 | DeSantis, Jr. |
| 6,491,683 B1 | 12/2002 | Dong et al. |
| 6,548,078 B2 | 4/2003 | Guo et al. |
| 6,719,751 B2 | 4/2004 | Dong et al. |
| 6,916,788 B2 | 7/2005 | Seo et al. |
| 7,563,255 B2 | 7/2009 | Adamis et al. |
| 2002/0119197 A1 | 8/2002 | Dyar et al. |
| 2003/0105121 A1 | 6/2003 | Bihari |
| 2004/0009222 A1 | 1/2004 | Chou et al. |
| 2004/0176341 A1 | 9/2004 | Chou et al. |
| 2010/0080830 A1 | 4/2010 | Ashton et al. |

FOREIGN PATENT DOCUMENTS

| | | |
|---|---|---|
| CN | 1200033 A | 11/1998 |
| EP | 0 147 780 A2 | 7/1985 |
| EP | 0 180 708 A1 | 5/1986 |
| EP | 0 316 838 A1 | 5/1989 |
| EP | 0 462 959 A1 | 12/1991 |
| EP | 0861659 A1 | 9/1998 |
| EP | 0891769 A1 | 1/1999 |
| HU | 210 461 A9 B3 | 4/1995 |
| JP | 58035110 A | 3/1983 |
| JP | 07-048246 A | 2/1995 |
| JP | 8253426 A | 10/1996 |
| JP | 10-182499 A | 7/1998 |
| TW | 396043 | 7/2000 |
| TW | 470655 | 1/2002 |

| WO | WO-84/00296 A1 | 2/1984 |
| WO | WO-91/11176 A1 | 8/1991 |
| WO | WO-92/07556 A1 | 5/1992 |
| WO | WO-9418956 A1 | 9/1994 |
| WO | WO-95/20567 A1 | 8/1995 |
| WO | WO-9535131 A1 | 12/1995 |
| WO | WO-97/11655 A1 | 4/1997 |
| WO | WO-97/15293 A2 | 5/1997 |
| WO | WO-98/42317 A2 | 10/1998 |
| WO | WO-98/43611 A1 | 10/1998 |
| WO | WO-99/11244 | 3/1999 |
| WO | WO-01/80825 A2 | 11/2001 |
| WO | WO-02/05788 | 1/2002 |
| WO | WO-02/87586 A1 | 11/2002 |
| WO | WO-03/094888 A1 | 11/2003 |

OTHER PUBLICATIONS

International Search Report for PCT/US01/12700 mailed Apr. 18, 2002.
International Search Report for PCT/US00/07513 mailed Aug. 30, 2000.
M. Kajhara, et al., "Development of a new drug delivery system for protein drugs using silicone (II)," Journal of Controlled Release, 73:279-291 (2001).
Yang et al., An Intravitreal Sustained-Release Triamcinolone and 5-Fluorouracil Codrug in the Treatment of Experimental Proliferative Vitreoretinopathy, Arch Opthalmol, 116:69-77 (1998).
Baker et al., In Vitro and In Vivo Evaluation of Intravitreal Sustained Release Dexamethasone Devices; IOVS 34(4): 121-122 (1993).
Barre-Sinoussi, et al., Science, 220:868-70 (1983).
Beer et al., Intraocular concentration and pharmacokinetics of triamcinolone acetonide after a single intravitreal injection; Ophthalmology 110(4): 681-6 (2003).
Blanford et al., 5-Fluorouracil Sustained Release Device Implantation: Toxicology and Histology in Rabbits, Invest. Opthal. and vis. Sci. 31(4):591, abstr. 2893-89 (1990). (Abstract).
Challa, et al. Exudative Macular Degeneration and Intravitreal Triamcinolone: 18 Month Follow Up. Australian and New Zealand Journal of Ophthalmology, 26(4):277-281 (1998).
Cheng et al., Intravitreal Sustained-Release Dexamethasone Device in the Treatment of Experimental Uveitis; Invest. Ophthal. & Visual Science 36(2): 442-453 (1995).
Dalgleish, et al., Nature, 312:763-67 (1984).
Database WPI, Week 7943, Derwent Publications Ltd., London, GB; AN 79-78139b XP002065720 & JP 54119 020 (Nippon Kayaku KK), Sep. 14, 1979 (Absract).
Driot et al., Ocular Pharmacokinetics of fluocinolone acetonide after Retisert intravitreal implantation in rabbits over a 1-year period; J Ocul Pharm. Ther 20(3): 269-75 (2004).
Gallo, et al., Science, 224:500-3 (1984).
Goins et al., "Intravitreal Sustained Release of Gancyclovir," Invest. Opthal. and Vis. Sci. 31(4):364, abstr. 1791 (1990). (Abstract).
Hainsworth et al., Sustained Release Intravitreal Dexamethasone; J. Ocular Pham and Ther. 12: 57-63 (1996).
Jaffe et al. Safety, Efficacy, and Pharmacokinetics of an Intravitreal, Fluocinolone Sustained Drug Delivery System. Investigative Ophthalmology & Visual Science. 40(4):S988. (1999).
Jaffe et al., Dexamethasone Sustained Drug Delivery Implant for the Treatment of Sever Uveitis; Brief Reports 20(4): 402-403 (2000).
Klatzmann, et al., Nature, 312:767-68 (1984).
Maddon, et al., Cell, 47:333-48 (1986).
Newell et al., Clearance and Metabolism of Intravitreal Triamcinolone; IOVS 34(4): 116 (1993).
Pearson et al. Clearance and Distribution of Ciprofloxacin After Intravitreal Injection. Retina. 13(4):326-330. (1993).
Pearson et al. Evaluation of a Delivery System Providing Long-Term Release of Cyclosporine. Arch Ophthamology. 114:311-17 (1996).
Pearson et al., "Polyvinyl Alcohol Membrane Permeability Characteristics of Gancyclovir," Invest. Opthal. and Vis. Sci. 30(4):511, abstr. 42 (1989). (Abstract).
Perasalo. The Prevalence of Macular Degeneration in a Cohort of Institutionalized Geriatric Glaucoma Patients. Acta Ophthamology. 72(2):175-77 (1994).
Rafii et al., Pharmacokinetics of Sustained-Release Implantable Devices of Acetazolamide; IOVA 34(4): 121-122 (1993).
Smith et al., "A Membrane Based Sustained Release Ocular Delivery System for 5-Fluorouracil," Invest. Opthal. and Vis. Sci. 30(4):271, abstr. 37 (1989) (Abstract).
Smith et al., "Intraocular Sustained Release of Antiviral Agents in AIDS," Proceed. Intern. Symp. Contol. Rel. Bioact. Mater. 17:470-471 (1990).
Smith et al., "Polyvinyl Alcohol Membrane Permeability Characteristics of 5-Fluorouracil," Journal of Ocular Pharmacology 4(2):147-152 (1988).
Solomon et al., "Sustained Release Drug Delivery Systems in Extracapsular Cataract Surgery," Invest. Opthal. and Vis. Sci. 31(4):351 Abstr. 1724-19 (1990) (Abstract).
Wu, X. S., Control Drug Delivery Systems (Part I), 1966, Technomic Publishing Co., Inc., pp. 32, 33, 44-46, 63, 66, and 67.
European Search Report for EP 08 16 1489 mailed Jun. 15, 2009.

METHOD FOR TREATING AND/OR PREVENTING RETINAL DISEASES WITH SUSTAINED RELEASE CORTICOSTEROIDS

CROSS REFERENCE TO RELATED APPLICATIONS

This application is a continuation of U.S. Ser. No. 11/635,161, filed Dec. 7, 2006, which is a continuation of U.S. Ser. No. 10/253,825, filed Sep. 25, 2002, which is a continuation of U.S. Ser. No. 09/735,636, filed Dec. 14, 2000, now U.S. Pat. No. 6,548,078, which is a continuation of U.S. Ser. No. 09/273,548, filed Mar. 22, 1999, now U.S. Pat. No. 6,217,895, the specifications of which are incorporated herein by reference in their entirety.

FIELD OF THE INVENTION

The present invention relates to the field of controlled pharmaceutical delivery, particularly to corticosteroids.

BACKGROUND OF THE INVENTION

Compounds classified as corticosteroids, such as triamcinolone, can effectively treat some forms of neovascularization such as corneal neovasularization. In general, corticosteroids have been unsuccessful in treating neovascularization of the posterior segment. In many patients, these compounds cause undesirable side effects. These adverse affects include elevations in intraocular pressure and the formation of, or acceleration of the development of cataracts. Elevations in intraocular pressure are of particular concern in patients who are already suffering from elevated intraocular pressure, such as glaucoma patients. Moreover, a risk exists that the use of corticosteroids in patients with normal intraocular pressure will cause elevations in pressure that result in damage to ocular tissue. Since therapy with corticosteroids is frequently long term, i.e., several days or more, a potential exists for significant damage to ocular tissue as a result of prolonged elevations in intraocular pressure attributable to that therapy.

One approach to solving the foregoing problems has been to search for specific compounds which are effective in treating neovascularization without elevating intraocular pressure. Another approach has been to administer corticosteroids in conjunction with another drug to "block" or reduce the IOP elevating effects of the corticosteroids or to treat IOP elevation separately with another drug. A further approach has been to intravitreally inject corticosteroids to treat ocular neovascularization.

There exists a need for an improved method for treating and/or preventing retinal diseases with corticosteroids.

DISCLOSURE OF THE INVENTION

An object of the present invention is to provide a method for treating and/or preventing ocular diseases which have neovascularization as a component with corticosteroids without the associated adverse side effects.

Additional objects, advantages and other features of the invention will be set forth in the description which follows and in part will become apparent to those having ordinary skill in the art upon examination of the following or may be learned from the practice of the invention. The objects and advantages of the invention may be realized and obtained as particularly pointed out in the appended claims.

According to the present invention, the foregoing and other objects are achieved in part by a method for administering a corticosteroid to a posterior segment of an eye, the method comprising the step of:

implanting a sustained release device to deliver the corticosteroid to the vitreous of the eye wherein aqueous corticosteroid concentration is less than vitreous corticosteroid concentration during release.

In accordance with the present invention, the foregoing and other advantages are also achieved in part by an implantable, sustained release device for administering a corticosteroid to a posterior segment of an eye, the device comprising:

a corticosteroid, wherein the device is configured to provide sustained release of the corticosteroid to the vitreous of the eye such that aqueous corticosteroid concentration remains less than vitreous corticosteroid concentration during the release.

Additional objects and advantages of the present invention will become readily apparent to those skilled in this art from the following detailed description, wherein embodiments of the invention are described simply by way of illustrating of the best mode contemplated in carrying out the invention. As will be realized, the invention is capable of other and different embodiments, and its several details are capable of modifications in various obvious respects, all without departing from the invention. Accordingly, the drawings and description are to be regarded as illustrative in nature and not as restrictive.

DESCRIPTION OF THE INVENTION

Figure 1:
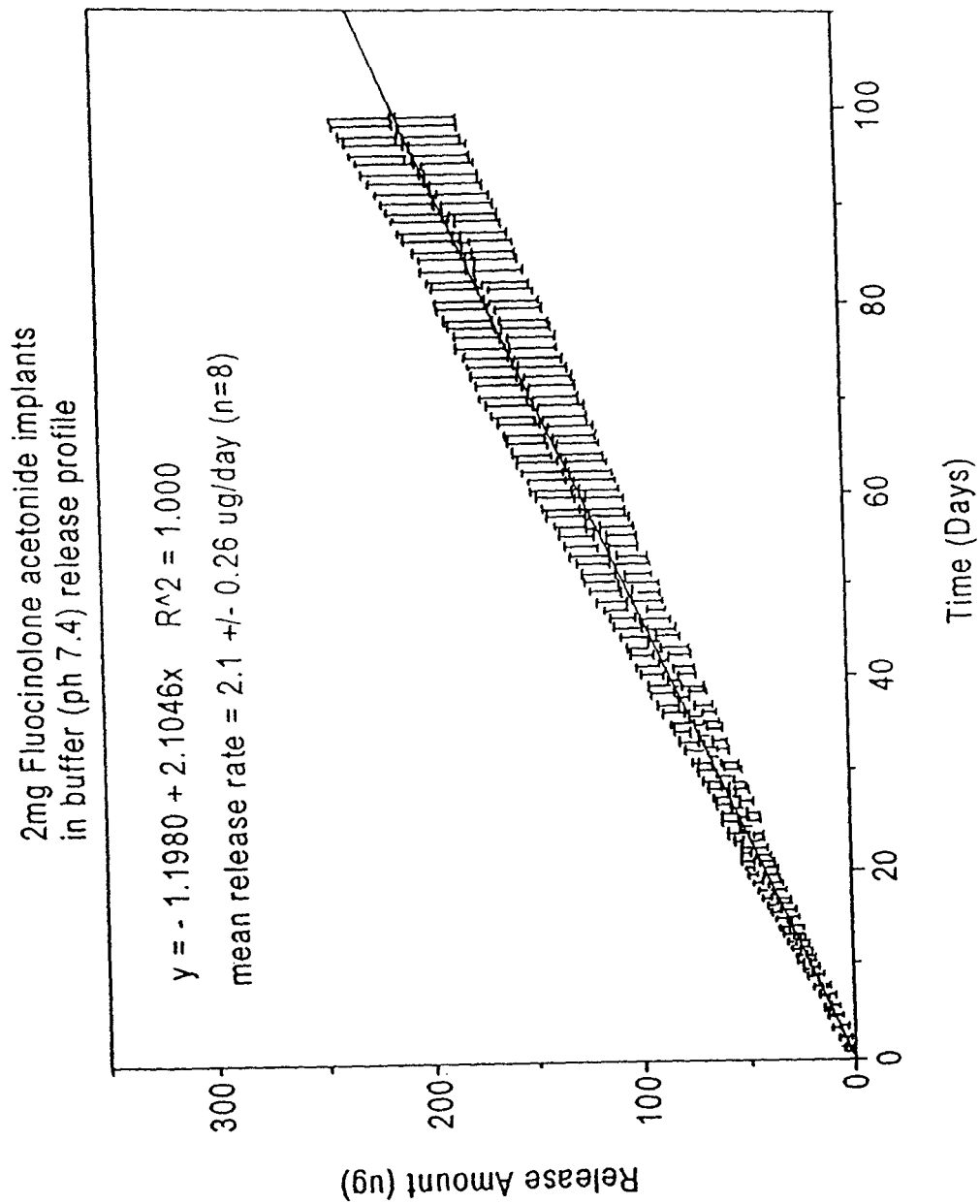
FIG. 1 shows the sustained release profile of a 2 mg fluocinolone acetonide implant in buffer.

The present invention provides a method for delivering a therapeutic amount of a corticosteroid to the vitreous of an eye but prevents toxic amounts of the corticosteroid from accumulating in the aqueous. The method comprises the step of implanting a sustained release device comprising a corticosteroid to the posterior segment to deliver the corticosteroid to the vitreous wherein aqueous corticosteroid concentration is less than vitreous corticosteroid concentration during release of the corticosteroid.

The present invention is particularly effective in treating diseases of the retina, retinal pigment epithelium (RPE) and choroid. These diseases include, for example, ocular neovascularization, ocular inflammation and retinal degenerations. Specific examples of these disease states include diabetic retinopathy, chronic glaucoma, retinal detachment, sickle cell retinopathy, senile macular degeneration, retinal neovascularization, subretinal neovascularization; rubeosis iritis inflammatory diseases, chronic posterior and pan uveitis, neoplasms, retinoblastoma, pseudoglioma, neovascular glaucoma; neovascularization resulting following a combined vitrectomy and lensectomy, vascular diseases retinal ischemia, choroidal vascular insufficiency, choroidal thrombosis, neovascularization of the optic nerve, diabetic macular edema, cystoid macular edema, macular edema, retinitis pigmentosa, retinal vein occlusion, proliferative vitreoretinopathy, angioid streak, and retinal artery occlusion, and, neovascularization due to penetration of the eye or ocular injury.

Examples of corticosteroids useful in the present invention include, for example, triamcinolone, dexamethasone, fluocinolone, cortisone, prednisolone, flumetholone, and derivatives thereof.

By "sustained release device" it is meant a device that releases drug over an extended period of time in a controlled fashion. Examples of sustained release devices useful in the present invention may be found in, for example, U.S. Pat. No. 5,378,475 and U.S. Pat. No. 5,773,019, and U.S. Ser. No. 08/919,221 filed on Aug. 28, 1997.

By "vitreous" of the eye, it is meant the vitreous or vitreal cavity of the eye. By "aqueous" of the eye, it is meant the aqueous humor of the eye.

In the present invention, a sustained release device is implanted into the eye such that it delivers corticosteroid to the posterior segment of the eye. In a preferred embodiment, the sustained release device is implanted intravitreally. However, the device may also be implanted in the choroidal space, sub-retinally, or in the sclera. These methods of administration and techniques for their preparation are well known by those of ordinary skill in the art. Methods of administration and techniques for their preparation are set forth in Remington's Pharmaceutical Sciences.

The aqueous corticosteroid concentration remains less than the vitreous corticosteroid concentration for substantially the lifetime of the sustained release device. Thus, during release of the corticosteroid, the aqueous corticosteroid concentration is about 0.002 µg/ml to about 0.01 µg/ml, such as from about 0.01 µg/ml to about 0.05 µg/ml. Preferably, the aqueous corticosteroid concentration is less than about 0.05 µg/ml.

Is contrast, during release of the corticosteroid, the vitreous corticosteroid concentration remains therapeutic, that is, less than about 10 µg/ml. The exact desired concentration depends upon the disease and therapeutic index of the drug.

The sustained release device useful in the present invention is any device which can be implanted to deliver corticosteroid to the vitreous of the eye and can release a corticosteroid for a sustained period of time, that is, for about 1 month to about 20 years, such as from about 6 months to about 5 years.

The sustained release device can be prepared to release the corticosteroid by pseudo zero order kinetics with a mean release rate of about 1 µg/day to about 50 µg/day, such as, about 1 µg/day to about 10 µg/day.

The following non-limiting examples are given by way of illustration only.

Example 1

Sustained release fluocinolone acetonide devices were implanted into the vitreous of 4 rabbits while animals in the control group received a sham operation. After implantation, all rabbits received a sub-retinal injection of gelatin microspheres releasing basic fibroblast growth factor. All control animals developed neovascularization while ¾ of the implant group showed no evidence of neovascularization. No animals showed any indication of ocular or systemic steroid-induced toxicity.

Example 2

Animals received intravitreal fluocinolone acetonide implants and were sacrificed at 1 month, 4 months, and 11 months. Samples of the vitreous and aqueous were collected for analysis by HPLC. Analysis was performed using a fully automated Hitachi HPLC system. The mobile phase was 40% acetonitrile buffered to a pH of 4.0. The flow rate was 1.0 ml/min with an Axxion C-18 column (25 cm×4 mm×5 µg/m) and UV detection at 238 nm. Intravitreal levels were found to be relatively constant throughout the study (0.1-0.2 µg/ml) while no steroid was detected in the aqueous humor (limit of detection 0.02 µg/ml).

DETAILED DESCRIPTION OF THE DRAWINGS

FIG. 1 shows the sustained release profile of a 2 mg fluocinolone acetonide implant in buffer over 100 days. The mean release rate was 2.1+/−0.26 µg/day.

Figure 2:
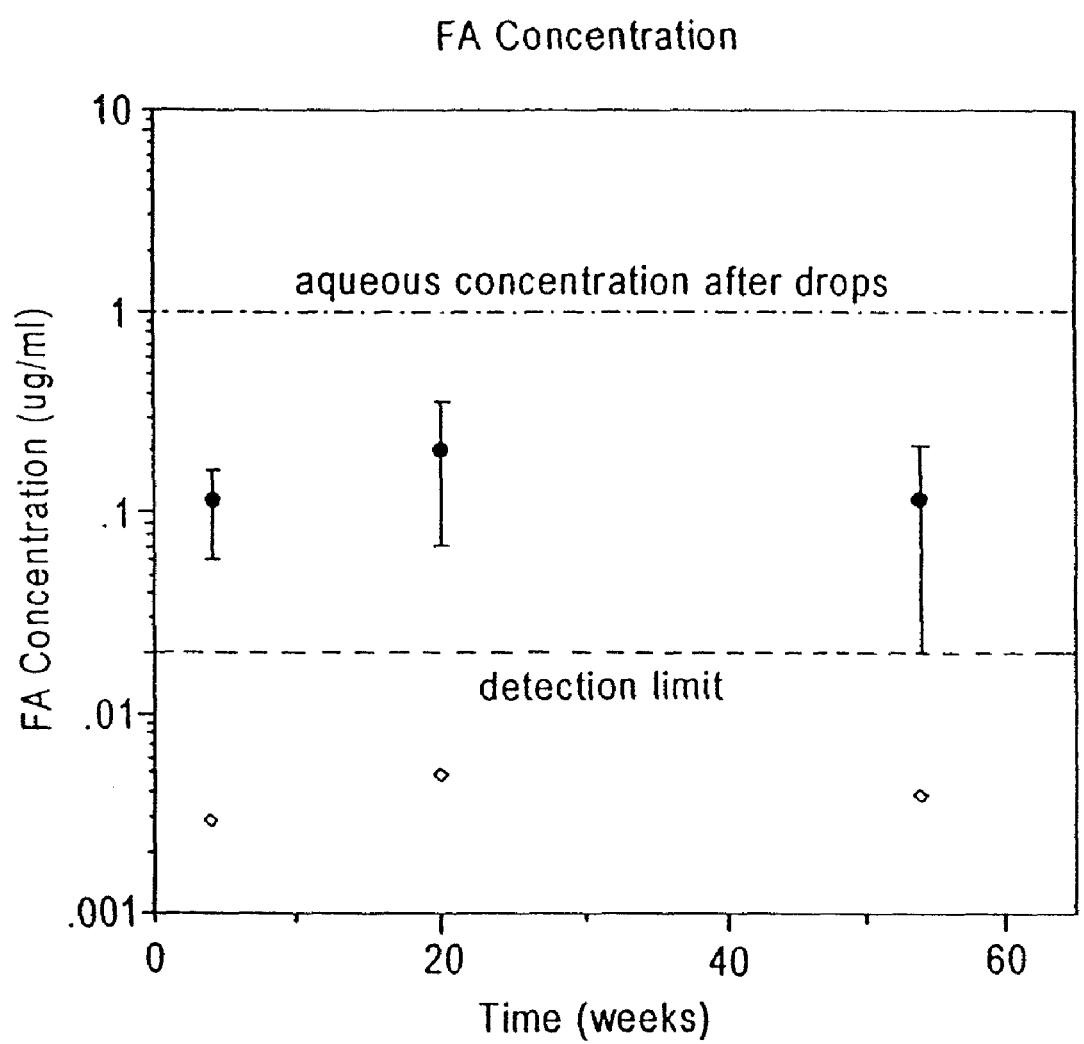
FIG. 2. shows the vitreous and aqueous levels of fluocinolone acetonide after implantation of a sustained release device.

FIG. 2 shows the vitreous and aqueous levels of fluocinolone acetonide after implantation of a sustained release device. Animals were sacrificed at 4 weeks, 20 weeks, and 1 year. FIG. 2 shows that therapeutic levels are maintained in the vitreous while drug levels in the aqueous humor were below the detection limit of the assay.

In the previous descriptions, numerous specific details are set forth, such as specific materials, structures, chemicals, processes, etc., in order to provide a better understanding of the present invention. However, the present invention can be practiced without resorting to the details specifically set forth. In other instances, well-known processing structures have not been described in detail in order not to unnecessarily obscure the present invention.

Only the preferred embodiment of the invention and but a few examples of its versatility are shown and described in the present disclosure. It is to be understood that the present invention is capable of use in various other combinations and environments and is capable of changes or modifications within the scope of the inventive concept as expressed herein. All patents, patent applications and publication cited herein are incorporated by reference in their entirety.

What is claimed is:

1. A sustained release device including fluocinolone acetonide (FA) disposed therein as the sole active agent, which device is dimensioned for implantation in the vitreal cavity of a patient's eye and configured to have a release rate over a time course of at least 4 weeks after implantation, which release rate results in an aqueous humor FA concentration less than one tenth the vitreous FA concentration.

2. A sustained release device including FA disposed therein as the sole active agent, which device is dimensioned for implantation in the vitreal cavity of a patient's eye and configured to have a release rate for said FA to produce a sustained and therapeutic concentration of said FA over a time course of at least 4 weeks effective for reducing neovascularization, edema, diabetic retinopathy, retinal detachment, sickle cell retinopathy, senile macular degeneration, retinal neovascularization, subretinal neovascularization, chronic posterior and pan uveitis, neovascularization resulting following a combined vitrectomy and lensectomy, vascular diseases retinal ischemia, choroidal vascular insufficiency, choroidal thrombosis, neovascularization of the optic nerve, diabetic macular edema, cystoid macular edema, macular edema, retinitis pigmentosa, retinal vein occlusion, proliferative vitreoretinopathy, angioid streak, or neovascularization due to penetration of the eye or ocular injury, which release rate results in an aqueous humor FA concentration which does not cause an increase in intraocular pressure over said time course that could result in damage to a patient's ocular tissue.

3. A sustained release device including FA disposed therein as the sole active agent, which device is dimensioned for implantation in the vitreal cavity of a patient's eye and configured to have a release rate for said FA to produce a sustained and therapeutic concentration of said FA over a time course of at least 4 weeks effective for reducing neovascularization, edema, or diabetic retinopathy, retinal detachment, sickle cell retinopathy, senile macular degeneration, retinal neovascularization, subretinal neovascularization, chronic posterior and pan uveitis, neovascularization resulting following a combined vitrectomy and lensectomy, vascular diseases retinal ischemia, choroidal vascular insufficiency, choroidal thrombosis, neovascularization of the optic nerve, diabetic macular edema, cystoid macular edema, macular edema, retinitis pigmentosa, retinal vein occlusion, proliferative vitreoretinopathy, angioid streak, or neovascularization due to penetration of the eye or ocular injury, which release rate results in an aqueous humor FA concentration less than one tenth the vitreous FA concentration.

4. The device of any of claims 1-3, wherein the aqueous humor FA concentration is less than about 0.05 μg/ml.

5. The device of any of claims 1-3, wherein the FA is released with pseudo zero order kinetics.

6. The device of any of claims 1-3, configured to have a release rate for said FA over said time course.

7. The device of any of claims 1-3, wherein said time course is at least 100 days.

8. The device of claim 1 or 3, which release rate results in an aqueous humor FA concentration which does not cause an increase in intraocular pressure over said time course that could result in damage to a patient's ocular tissue.

9. The device of claim 8, wherein the release rate for said FA over said time course is effective for reducing one or more of senile macular degeneration, chronic posterior or and pan uveitis, or diabetic macular edema.

10. The device of any of claims 1-3, which release rate does not produce ocular steroid-induced toxicity.

11. The device of claim 2 or 3, which device is effective for reducing senile macular degeneration, chronic posterior or pan uveitis, or diabetic macular edema.

12. A sustained release device including a steroid disposed therein as the sole active agent, which device is dimensioned for implantation in the vitreal cavity of a patient's eye and configured to release a therapeutically effective amount of steroid, which amount does not produce ocular or systemic steroid-induced toxicity.

13. A sustained release device including a steroid disposed therein as the sole active agent, which device is dimensioned for implantation in the posterior segment of a patient's eye and configured to release a therapeutically effective amount of steroid, which amount does not produce ocular or systemic steroid-induced toxicity.

14. The device of claim 12 or 13, wherein the steroid is released with pseudo zero order kinetics.

15. A sustained release device including FA disposed therein as the sole active agent, which device is dimensioned for implantation in the posterior segment of a patient's eye and configured to have a release rate over a time course of at least 4 weeks after implantation, which release rate results in an aqueous humor FA concentration less than one tenth the vitreous FA concentration.

16. A sustained release device including FA disposed therein as the sole active agent, which device is dimensioned for implantation in the posterior segment of a patient's eye and configured to have a release rate for said FA to produce a sustained and therapeutic concentration of said FA over a time course of at least 4 weeks effective for reducing neovascularization, edema, diabetic retinopathy, retinal detachment, sickle cell retinopathy, senile macular degeneration, retinal neovascularization, subretinal neovascularization, chronic posterior and pan uveitis, neovascularization resulting following a combined vitrectomy and lensectomy, vascular diseases retinal ischemia, choroidal vascular insufficiency, choroidal thrombosis, neovascularization of the optic nerve, diabetic macular edema, cystoid macular edema, macular edema, retinitis pigmentosa, retinal vein occlusion, proliferative vitreoretinopathy, angioid streak, or neovascularization due to penetration of the eye or ocular injury, which release rate results in an aqueous humor FA concentration which does not cause an increase in intraocular pressure over said time course that could result in damage to a patient's ocular tissue.

17. A sustained release device including FA disposed therein as the sole active agent, which device is dimensioned for implantation in the posterior segment of a patient's eye and configured to have a release rate for said FA to produce a sustained and therapeutic concentration of said FA over a time course of at least 4 weeks effective for reducing neovascularization, edema, diabetic retinopathy, retinal detachment, sickle cell retinopathy, senile macular degeneration, retinal neovascularization, subretinal neovascularization, chronic posterior and pan uveitis, neovascularization resulting following a combined vitrectomy and lensectomy, vascular diseases retinal ischemia, choroidal vascular insufficiency, choroidal thrombosis, neovascularization of the optic nerve, diabetic macular edema, cystoid macular edema, macular edema, retinitis pigmentosa, retinal vein occlusion, proliferative vitreoretinopathy, angioid streak, or neovascularization due to penetration of the eye or ocular injury, which release rate results in an aqueous humor FA concentration less than one tenth the vitreous FA concentration.

18. The device of any of claims 15-17, wherein the aqueous humor FA concentration is less than about 0.05 μg/ml.

19. The device of any of claims 15-17, wherein the FA is released with pseudo zero order kinetics.

20. The device of any of claims 15-17, configured to have a release rate for said FA over said time course.

21. The device of any of claims 15-17, wherein said time course is at least 100 days.

22. The device of claim 15 or 17, which release rate results in an aqueous humor FA concentration which does not cause an increase in intraocular pressure over said time course that could result in damage to a patient's ocular tissue.

23. The device of claim 22, wherein the release rate for said FA over said time course is effective for reducing one or more of senile macular degeneration, chronic posterior or and pan uveitis, or diabetic macular edema.

24. The device of any of claims 15-17, which release rate does not produce ocular steroid-induced toxicity.

25. The device of claim 16 or 17, which device is effective for reducing senile macular degeneration, chronic posterior or pan uveitis, or diabetic macular edema.

* * * * *